(12) United States Patent
Crossman et al.

(10) Patent No.: US 10,898,636 B2
(45) Date of Patent: Jan. 26, 2021

(54) NEEDLE TIP STORAGE AND REMOVAL DEVICE

(71) Applicant: OWEN MUMFORD LIMITED, Oxford (GB)

(72) Inventors: David Danvers Crossman, Oxford (GB); Steven Mark Guy Rolfe, Oxford (GB)

(73) Assignee: Owen Mumford Limited, Oxford (GB)

( * ) Notice: Subject to any disclaimer, the term of this patent is extended or adjusted under 35 U.S.C. 154(b) by 45 days.

(21) Appl. No.: 16/152,164

(22) Filed: Oct. 4, 2018

(65) Prior Publication Data

US 2019/0030258 A1 Jan. 31, 2019

Related U.S. Application Data

(63) Continuation of application No. 12/300,525, filed as application No. PCT/GB2007/001712 on May 10, 2007, now abandoned.

(30) Foreign Application Priority Data

May 11, 2006 (GB) .................................. 0609308.2

(51) Int. Cl.
*A61M 5/00* (2006.01)
*A61M 5/32* (2006.01)
(Continued)

(52) U.S. Cl.
CPC ......... *A61M 5/002* (2013.01); *A61B 50/3001* (2016.02); *A61B 50/362* (2016.02); *A61M 5/321* (2013.01); *A61M 5/3202* (2013.01); *A61M 5/3205* (2013.01); *A61M 5/3213* (2013.01); *A61M 5/3293* (2013.01);
(Continued)

(58) Field of Classification Search
CPC .. A61M 5/002; A61M 5/3202; A61M 5/3205; A61M 5/321; A61M 5/3213; A61M 5/3276; A61M 5/3293; A61M 5/347; A61M 5/5086; A61M 2005/3208;
(Continued)

(56) References Cited

U.S. PATENT DOCUMENTS 5,026,345 A 6/1991 Teringo
5,554,129 A * 9/1996 Stevenson ........... A61M 5/3213
604/110

(Continued)

FOREIGN PATENT DOCUMENTS

WO 2005011781 A1 2/2005

OTHER PUBLICATIONS

First Examination Report issued in corresponding Indian Patent Application No. 9621/DELNP/2008, dated May 3, 2017, 8 pages.
(Continued)

*Primary Examiner* — Shefali D Patel
(74) *Attorney, Agent, or Firm* — Quarles & Brady LLP

(57) ABSTRACT

A needle tip storage and removal device comprises a storage compartment having a splined socket which engages complementary splines on a needle tip collar, the storage compartment being sealed by a peelable foil. Alongside the storage compartment is a removal compartment having a drive socket of similar configuration. The device assists safe removal and disposal of a used needle prior to fitting a new needle.

6 Claims, 1 Drawing Sheet

(51) Int. Cl.
*A61B 50/36* (2016.01)
*A61B 50/30* (2016.01)
*A61M 5/34* (2006.01)
*A61M 5/50* (2006.01)

(52) U.S. Cl.
CPC ..... *A61M 5/347* (2013.01); *A61B 2050/3008* (2016.02); *A61M 5/5086* (2013.01); *A61M 2005/3208* (2013.01)

(58) Field of Classification Search
CPC .. A61M 2005/3215; A61M 2005/3206; A61B 50/3001; A61B 50/362; A61B 2050/3008
See application file for complete search history.

(56) References Cited

U.S. PATENT DOCUMENTS

| | | |
|---|---|---|
| 6,986,760 B2 | 1/2006 | Giambattista et al. |
| 2006/0032769 A1* | 2/2006 | Erickson ............... A61M 5/002 206/365 |

OTHER PUBLICATIONS

Second Office Action issued in corresponding Indian Patent Application No. 9621/DELNP/2008, dated Mar. 25, 2019, 3 pages.

\* cited by examiner

NEEDLE TIP STORAGE AND REMOVAL DEVICE

This application is a continuation of U.S. patent application Ser. No. 12/300,525 filed Nov. 12, 2008, which is a 35 U.S.C. § 371 national stage of International application PCT/GB2007/001712 filed May 10, 2007, which claims priority to Great Britain application 0609308.2 filed May 11, 2006. The entire contents of each of the above-identified applications are hereby incorporated by reference.

FIELD OF THE INVENTION

This invention relates to a needle tip storage and removal device and in particular, but not exclusively, to a device for use with an injection device intended to inject a number of metered doses from a cartridge of therapeutic material.

BACKGROUND OF THE INVENTION

In a conventional pen injector such as the Owen Mumford Autopen®, a cartridge of therapeutic substance is loaded into the cartridge holder and a single use needle tip is screwed onto the forward end of the device. The needle tip has a double-ended needle, the rear end of which penetrates a rubber membrane in the forward end of the cartridge as the needle tip is screwed on. A metered dose can then be dialed into the pen injector, the needle pushed into the injection site, and the trigger on the device actuated to inject the metered dose. After the injection, the needle tip should be removed from the device and discarded.

In many conventional arrangements, the exterior of the needle tip hub is provided with splines and the needle tip is supplied in a foil-sealed container, having a complementary splined socket in which the needle hub is supplied. To use such a needle tip, the foil is removed and the needle, whilst still shrouded by the container is screwed onto the injection device using the container as a spanner. Once fully home, the container may be withdrawn axially leaving the needle exposed, although in some instances a removable secondary needle shield is provided. Following injection, the user may slide the container back onto the needle hub and use it as a spanner to remove the needle tip. The needle tip can then be safely discarded because the used needle is now re-enclosed by the container. This system works extremely well provided the user retains the container and uses it to remove the needle tip immediately after the injection. However, in many instances, users may not follow the recommendation to change the needle tip after each injection and may instead use the same needle tip for several injections over an extended period. In this case they may have discarded the original container and so may be left to remove the needle tip by unscrewing it whilst the needle is still exposed. This provides a risk of needle stick injury both whilst removing the needle tip and when it is discarded. Alternatively, they may inject themselves and then leave the needle in place, covering it with the device cap, and then remove the needle only when they wish to replace with a new needle. Again, this poses a risk of needle stick injury.

We have designed an arrangement to reduce these risks.

SUMMARY OF THE INVENTION

Accordingly, some embodiments of this invention provide a needle tip storage comprising first and second ends defined on opposite sides of the device, a storage compartment defined in the device and configured to receive a needle tip, a removal compartment defined in the device configured to receive the needle tip, and the needle tip received in the storage compartment, Other embodiments of the invention provides a removable sealing element disposed on the first end of the device and configured to seal the storage compartment.

Other embodiments of the invention provides a snap lock in the removal compartment configured to permanently capture the needle tip received in the disposal compartment.

According to another embodiment of the invention, a device for storing a needle tip is provided comprising a threaded collar having splines formed in an external surface thereof. A double-ended needle located in the threaded collar such that a forward part of the double-ended needle projects from a forward part of the threaded collar. A rearward part of the double-ended needle extends towards a rearward part of the threaded collar such that the rearward part of the double-ended needle does not project beyond a rearward surface of the threaded collar. The device comprises first and second ends defined on opposite sides of the device, a storage compartment defined in the device and configured to receive a needle tip, a removal compartment defined in the device configured to receive the needle tip, and the needle tip received in the storage compartment.

According to a method of the invention, changing a needle tip on a pen injector comprises: providing a pen injector having a first removable needle tip, providing a needle tip storage device, sliding the disposal compartment over the first removable needle tip on the pen injector, turning the pen injector and device to unscrew the first removable needle tip, inserting the pen injector into the second needle tip in the storage compartment, turning the pen injector and device to screw the second needle tip onto the injector device, and withdrawing the second needle tip from the storage compartment when screwed onto the pen injector.

BRIEF DESCRIPTION OF THE DRAWINGS

Whilst the invention has been described above, it extends to any inventive combination of the features set out above, or in the following description or claims.

The invention may be performed in various ways, and an embodiment thereof will now be described by way of example only, reference being made to the accompanying drawings, in which.

DETAILED DESCRIPTION OF THE INVENTION

Figure 1:
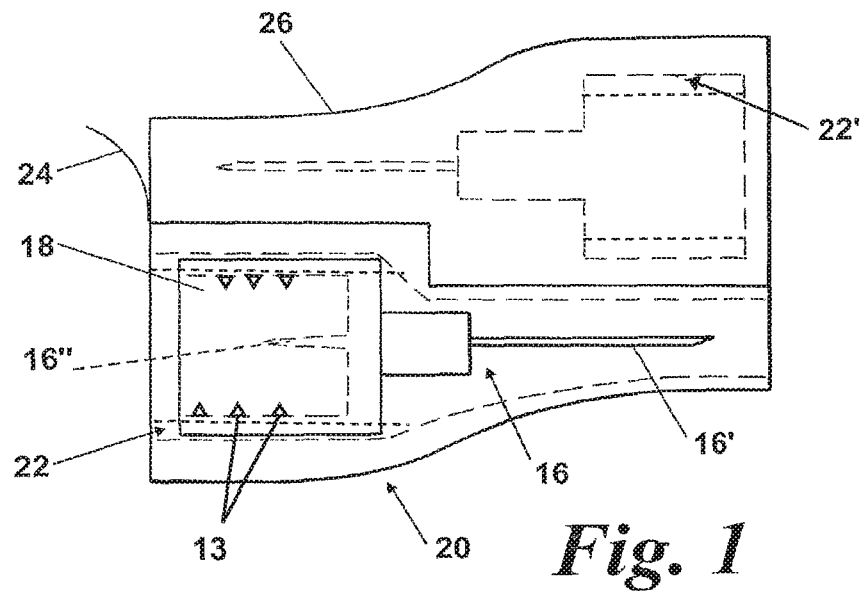
FIG. 1 is a schematic top plan view of a needle tip storage and removal device in accordance with this invention.
Figure 2:
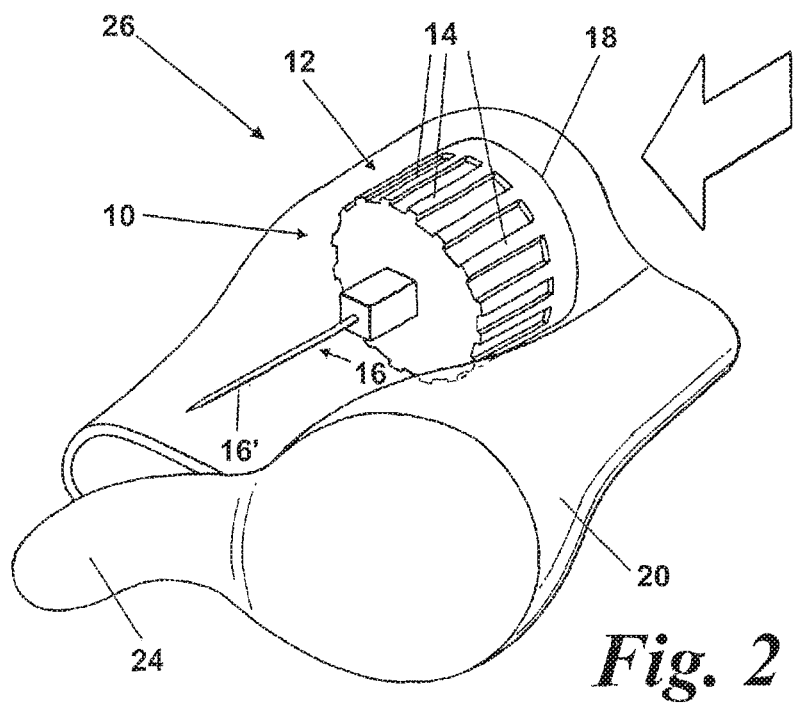
FIG. 2 is a general perspective view of the device of FIG. 1 with a used needle tip in the removal compartment.

The device illustrated in the Figures is intended to store a needle tip 10 for being screwed onto the end of a pen injector type device, and to remove the needle tip after use and to shield the forward part of the needle after use.

The needle tip may be a Unifine® pen tip. The pen tip comprises a threaded collar 12 having an internally threaded portion 13 and external splines 14 with a double ended needle 16 having a forward part 16' projecting forwardly of the collar 18 and a rearward part 16" extending rearwardly but not projecting beyond the rearward surface of the collar. The device in this embodiment includes a storage compartment 20 having a complementarily splined sockets 22 into which the drive collar can be slid with the needle guarded by the distal end of the compartment 20. The storage compartment 20 is sealed by a peelable sealing foil element 24. Alongside the storage compartment 20 is a removal compartment 26 which also has a complementarily splined socket 22' and a needle shrouding portion and is generally similar to the configuration of the storage compartment, although the removal compartment may be designed to have snap lock means or the like to permanently capture the used needle tip.

In use, assuming that the pen injector already has a used needle attached, the removal compartment 26 is slid over the used needle and turned to unscrew the needle tip and to leave it in the removal compartment, with the used exposed needle shrouded by the compartment. Having done this, the foil 24 may be peeled off the storage compartment 20 and the new needle tip 10 screwed onto the device. The needle tip storage and removal device can then be discarded.

What is claimed is:

1. A needle tip storage device, comprising:
   first and second ends defined on opposite sides of the device;
   a storage compartment defined in the device and configured to receive a needle tip, the storage compartment comprising an internal surface defining a splined socket extending from an opening defined in the first end of the device to a shroud at a distal end located towards the second end of the device, wherein a part of the device surrounding the splined socket of the storage compartment is of larger outside dimensions than a part of the device surrounding the shroud of the storage compartment;
   a removal compartment defined in the device configured to receive the needle tip, the removal compartment comprising an internal surface defining a splined socket extending from an opening defined in the second end of the device to a shroud at a distal end located towards the first end of the device, wherein a part of the device surrounding the splined socket of the removal compartment is of larger outside dimensions than a part of the device surrounding the shroud of the removal compartment; and
   the needle tip received in the storage compartment, the needle tip comprising a threaded collar having splines formed in an external surface thereof, a double-ended needle located in the threaded collar such that a forward part of the double-ended needle projects from a forward part of the threaded collar, and a rearward part of the double-ended needle extends towards a rearward part of the threaded collar such that the rearward part of the double-ended needle does not project beyond a rearward surface of the threaded collar, such that the forward part of the double-ended needle is positioned within the shroud of the storage compartment;
   wherein the splined socket of the storage compartment and the splined socket of the removal compartment are a same size and are complementary to the splines of the needle tip.

2. The needle tip storage device as claimed in claim 1, further comprising a removable sealing element disposed on the first end of the device and configured to seal the storage compartment.

3. The needle tip storage device as claimed in claim 1, wherein the splines of the threaded collar extend continuously around the external surface thereof.

4. A device for storing a needle tip comprising a threaded collar having splines formed in an external surface thereof, a double-ended needle located in the threaded collar such that a forward part of the double-ended needle projects from a forward part of the threaded collar, and a rearward part of the double-ended needle extends towards a rearward part of the threaded collar such that the rearward part of the double-ended needle does not project beyond a rearward surface of the threaded collar, the device comprising:
   first and second ends defined on opposite sides of the device;
   a storage compartment defined in the device and configured to receive the needle tip, the storage compartment comprising an internal surface defining a splined socket extending from an opening defined in the first end of the device to a shroud at a distal end located towards the second end of the device, wherein a part of the device surrounding the splined socket of the storage compartment is of larger outside dimensions than a part of the device surrounding the shroud of the storage compartment; and
   a removal compartment defined in the device configured to receive the needle tip, the removal compartment comprising an internal surface defining a splined socket extending from an opening defined in the second end of the device to a shroud at a distal end located towards the first end of the device, wherein a part of the device surrounding the splined socket of the removal compartment is of larger outside dimensions than a part of the device surrounding the shroud of the removal compartment;
   wherein the splined socket of the storage compartment and the splined socket of the removal compartment are a same size and are complementary to the splines of the needle tip.

5. The device for storing the needle tip as claimed in claim 4, further comprising a removable sealing element disposed on the first end and configured to seal the storage compartment.

6. The device for storing the needle tip as claimed in claim 4, wherein the splines of the threaded collar extend continuously around the external surface thereof.

* * * * *